United States Patent
Kim (10) Patent No.: US 11,020,325 B2
(45) Date of Patent: Jun. 1, 2021

(54) EXTERNAL PREPARATION FOR SKIN OR PASTE INCLUDING AEROGEL HAVING BOTH HYDROPHILICITY AND HYDROPHOBICITY

(71) Applicant: Industry-University Cooperation Foundation Hanyang University, Seoul (KR)

(72) Inventor: Tae-Won Kim, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 362 days.

(21) Appl. No.: 15/769,581

(22) PCT Filed: Oct. 21, 2016

(86) PCT No.: PCT/KR2016/011867
§ 371 (c)(1),
(2) Date: Apr. 19, 2018

(87) PCT Pub. No.: WO2017/069547
PCT Pub. Date: Apr. 27, 2017

(65) Prior Publication Data
US 2018/0303724 A1 Oct. 25, 2018

(30) Foreign Application Priority Data

Oct. 21, 2015 (KR) .................. 10-2015-0146762
Sep. 5, 2016 (KR) .................. 10-2016-0113950

(51) Int. Cl.
*A61K 8/02* (2006.01)
*A61K 8/25* (2006.01)
(Continued)

(52) U.S. Cl.
CPC ............ *A61K 8/022* (2013.01); *A61K 8/0279* (2013.01); *A61K 8/042* (2013.01); *A61K 8/06* (2013.01);
(Continued)

(58) Field of Classification Search
CPC . A61K 8/25; A61K 8/89; A61K 8/585; A61K 2800/612; A61K 2800/651; A61K 8/022; A61Q 19/00; A61Q 19/007
See application file for complete search history.

(56) References Cited

U.S. PATENT DOCUMENTS 6,280,744 B1   8/2001  Schwertfeger et al.
6,365,638 B1 * 4/2002  Schwertfeger ........... A61K 8/02
                                                516/100
(Continued)

FOREIGN PATENT DOCUMENTS

CN        1175904 A      3/1998
DE   10 2011 018171 A1  10/2012
(Continued)

OTHER PUBLICATIONS

International Search Report for PCT/KR2016/011867 dated Dec. 8, 2016 [PCT/ISA/210].
(Continued)

*Primary Examiner* — Kortney L. Klinkel
(74) *Attorney, Agent, or Firm* — Sughrue Mion, PLLC (57) ABSTRACT

An external preparation for skin and an aerogel paste are provided. The external preparation for skin comprises aerogel powder and a solvent. The aerogel powder includes a mixture of aerogel particles having a hydrophilic functional group on a surface thereof and aerogel particles having a hydrophobic functional group on a surface thereof. The hydrophilic functional group is a hydroxy group, and the hydrophobic functional group is hydrogen, a C1 to C18 alkyl
(Continued)

(a)

(b)

(c)

group, a silyloxy group represented by the following Chemical Formula 1, or a combination thereof: [Chemical Formula 1] *—$OSiH_{(3-n)}R^1_n$ wherein R1 is a C1 to C18 alkyl group, n is an integer ranging from 0 to 3, and * denotes a bond.

11 Claims, 6 Drawing Sheets

(51) Int. Cl.
    *A61Q 19/00*     (2006.01)
    *A61K 8/04*     (2006.01)
    *A61K 8/89*     (2006.01)
    *A61K 8/06*     (2006.01)
    *A61K 8/58*     (2006.01)

(52) U.S. Cl.
    CPC ................ *A61K 8/25* (2013.01); *A61K 8/585* (2013.01); *A61K 8/89* (2013.01); *A61Q 19/00* (2013.01); *A61Q 19/007* (2013.01); *A61K 2800/28* (2013.01); *A61K 2800/612* (2013.01); *A61K 2800/614* (2013.01); *A61K 2800/651* (2013.01); *A61K 2800/81* (2013.01)

(56) References Cited

U.S. PATENT DOCUMENTS

| | | |
|---|---|---|
| 7,674,476 B1 | 3/2010 | Schwertfeger et al. |
| 2001/0034375 A1 | 10/2001 | Schwertfeger et al. |
| 2006/0286360 A1 | 12/2006 | Rhine et al. |
| 2008/0188575 A1 | 8/2008 | Gaspar Martinho et al. |
| 2014/0134219 A1 | 5/2014 | Bonner et al. |

FOREIGN PATENT DOCUMENTS

| | | |
|---|---|---|
| JP | 2661638 B2 | 10/1997 |
| JP | 11-500441 A | 1/1999 |
| JP | 11-505499 A | 5/1999 |
| KR | 10-1420163 B | 7/2014 |
| WO | 2013/190130 A1 | 12/2013 |

OTHER PUBLICATIONS

H. El Rassy, et al., "Surface Characterization of Silica Aerogels with Different Proportions of Hydrophobic Groups, Dried by the $CO_2$ Supercritical Method", Langmuir, 2003, 19, pp. 358-363.

* cited by examiner

EXTERNAL PREPARATION FOR SKIN OR PASTE INCLUDING AEROGEL HAVING BOTH HYDROPHILICITY AND HYDROPHOBICITY

CROSS REFERENCE TO RELATED APPLICATIONS

This application is a National Stage of International Application No. PCT/KR2016/011867, filed on Oct. 21, 2016, which claims priority from Korean Patent Application No. 10-2015-0146762, filed on Oct. 21, 2015 and 10-2016-0113950, filed on Sep. 5, 2016.

TECHNICAL FIELD

The present invention relates to a composition including aerogel, and more particularly, to an external preparation for skin including aerogel.

BACKGROUND ART

Aerogel that was first created in 1931 is a porous ultralight material, in which the liquid component of the gel has been replaced with a gas, and is known to be made of metal oxides such as silica, alumina, titania, zirconia, iron oxides, or the like, carbon, or agar. Metal oxide aerogels are typically synthesized by using a sol-gel process.

Aerogel exhibits heat shielding, sound insulation, electromagnetic wave shielding capability, and the like due to its high microporosity, and thus is being used in various industrial fields including heat insulating materials for construction and acoustic delay materials (U.S. Pat. No. 6,136,216 and US 2010/0275617).

DISCLOSURE

Technical Problem

The present invention is directed to providing an external preparation for skin including aerogel, and particularly, an external preparation for skin or a paste having improved moisturizing performance.

Technical Solution

According to an embodiment of the present invention, an external preparation for skin is provided. The external preparation for skin comprises aerogel powder and a solvent. The aerogel powder includes a mixture of aerogel particles having a hydrophilic functional group on a surface thereof and aerogel particles having a hydrophobic functional group on a surface thereof. The hydrophilic functional group is a hydroxy group, and the hydrophobic functional group is hydrogen, a C1 to C18 alkyl group, a silyloxy group represented by the following Chemical Formula 1, or a combination thereof:

[Chemical Formula 1]

wherein R1 is a C1 to C18 alkyl group, n is an integer ranging from 0 to 3, and * denotes a bond.

In a specific embodiment, The aerogel powder may include a mixture of hydrophilic aerogel particles and hydrophobic aerogel particles. The aerogel powder may contain 30 to 70 wt % of the hydrophilic aerogel particles and 30 to 70 wt % of the hydrophobic aerogel particles. The aerogel powder may further include hybrid aerogel particles having both the hydrophilic functional group and the hydrophobic functional group on a surface thereof. The hybrid aerogel particles may have the hydrophobic functional group and the hydrophilic functional group on a surface thereof at a molar ratio of 8:2 to 2:8. The aerogel powder may contain 25 to 40 wt % of the hybrid aerogel particles, 25 to 40 wt % of the hydrophilic aerogel particles, and 25 to 40 wt % of the hydrophobic aerogel particles.

In another specific embodiment, the aerogel powder may include hybrid aerogel particles having both the hydrophilic functional group and the hydrophobic functional group on a surface thereof. The hydrophobic functional group may be a silyloxy group represented by Chemical Formula 1, wherein n may be an integer ranging from 1 to 3, and the C1 to C18 alkyl group may be a C1 to C6 linear alkyl group. The C1 to C6 linear alkyl group may be a methyl group or an ethyl group.

The external preparation for skin may further comprises at least one selected from the group consisting of a thickener, a moisturizer, a preservative, and a surfactant. The external preparation for skin may be a moisturizing cream or a peel-off type pack.

According to another embodiment of the present invention, an aerogel paste is provided. The aerogel paste comprises aerogel powder exhibiting all of a Si—O—Si group, a Si—CH$_3$ group, and an OH group in a Fourier transform infrared (FT-IR) spectroscopic graph, and a solvent.

The aerogel powder may be formed by mixing hydrophobic aerogel particles having a Si—CH$_3$ group on a surface thereof and hydrophilic aerogel particles having an OH group on a surface thereof. The aerogel powder may contain 30 to 70 wt % of the hydrophilic aerogel particles and 30 to 70 wt % of the hydrophobic aerogel particles. The aerogel powder may further include hybrid aerogel particles having both a Si—CH$_3$ group and an OH group on a surface thereof. The aerogel powder may contain 25 to 40 wt % of the hybrid aerogel particles, 25 to 40 wt % of the hydrophobic aerogel particles, and 25 to 40 wt % of the hydrophilic aerogel particles.

The solvent may be water, an alcohol, or a combination thereof.

According to still another embodiment of the present invention, a method of preparing an external preparation for skin is provided. The method comprises mixing aerogel powder formed by mixing aerogel particles having a hydrophilic functional group on a surface thereof and aerogel particles having a hydrophobic functional group on a surface thereof with a solvent to obtain an aerogel paste. The hydrophilic functional group is a hydroxy group, and the hydrophobic functional group is hydrogen, a C1 to C18 alkyl group, a silyloxy group represented by the following Chemical Formula 1, or a combination thereof:

[Chemical Formula 1]

wherein R$^1$ is a C1 to C18 alkyl group, n is an integer ranging from 0 to 3, and * denotes a bond.

In a specific embodiment, the aerogel powder may be prepared by converting hydrophobic aerogel powder into hydrophilic aerogel powder through thermal treatment under an oxidation atmosphere; and then mixing the hydrophilic aerogel powder with the hydrophobic aerogel powder.

In another specific embodiment, the aerogel powder may be prepared by thermally treating hydrophobic aerogel powder under an oxidation atmosphere in such a way that some particles of the hydrophobic aerogel powder are converted into hybrid aerogel particles having both a hydrophilic functional group and a hydrophobic functional group on a surface thereof, some of the other particles are converted into hydrophilic aerogel particles, and the rest of the other particles remain as hydrophobic aerogel particles.

Advantageous Effects

According to the present invention, an external preparation for skin having an excellent moisturizing effect can be achieved. Also, the external preparation for skin can improve effects of sebum removal and skin texture improvement.

However, effects of the present invention are not limited to the above-described effects and other unmentioned effects may be clearly understood by those skilled in the art from the following descriptions.

DESCRIPTION OF DRAWINGS

Example embodiments of the present invention will become more apparent by describing in detail example embodiments of the present invention with reference to the accompanying drawings, in which.

MODES OF THE INVENTION

Hereinafter, exemplary embodiments according to the present invention will be described in further detail with reference to the accompanying drawings for the purpose of more specifically describing the present invention. However, the present invention can be embodied in various forms without being limited to the embodiments.

In the specification, when the expression "Cx to Cy" is used, it should be understood that all integer carbon numbers between x and y are should be interpreted as described.

In the specification, when the expression "x to y" is used, it should be understood that all numbers between x and y are should be interpreted as described.

The term "aerogel" used herein may refer to a gel in which a gas is used as a dispersion medium. The aerogel may be classified into aerogel in a narrow sense and a xerogel according to conditions for drying a liquid contained in a gel. The aerogel in a narrow sense may be formed by removing a liquid contained in a gel at or above a critical temperature and at or above a critical pressure, and the xerogel may be formed by removing a liquid contained in a gel at or below a critical point.

The term "aerogel powder" used herein may have a plurality of particles. Also, the aerogel powder may be silica aerogel powder.

Aerogel Powder Example 1

At least some particles of aerogel powder according to an embodiment of the present invention may be hybrid aerogel particles having both a hydrophobic surface and a hydrophilic surface. In other words, the aerogel powder may include hybrid aerogel particles having both a hydrophobic surface and a hydrophilic surface. The hybrid aerogel particles may also have both hydrophobicity and hydrophilicity at a surface of a pore inside the particle as well as at a surface of the particle.

In addition, the aerogel powder may further include hydrophobic aerogel particles having a hydrophobic surface, hydrophilic aerogel particles having a hydrophilic surface, or a combination thereof. The hydrophobic aerogel particles may have hydrophobicity at a surface of a pore inside the particle as well as at a surface of the particle, and the hydrophilic aerogel particles may have hydrophilicity at a surface of a pore inside the particle as well as at a surface of the particle.

In one example, the aerogel powder may be a mixture including all of hydrophilic aerogel particles, hydrophobic aerogel particles, and hybrid aerogel particles. This mixture may contain about 25 to 40 wt % of the hybrid aerogel particles, about 25 to 40 wt % of the hydrophilic aerogel particles, and about 25 to 40 wt % of the hydrophobic aerogel particles. In one embodiment, the hybrid aerogel particles, the hydrophilic aerogel particles, and the hydrophobic aerogel particles may be contained in a weight ratio of 1:1:1.

Figure 1:
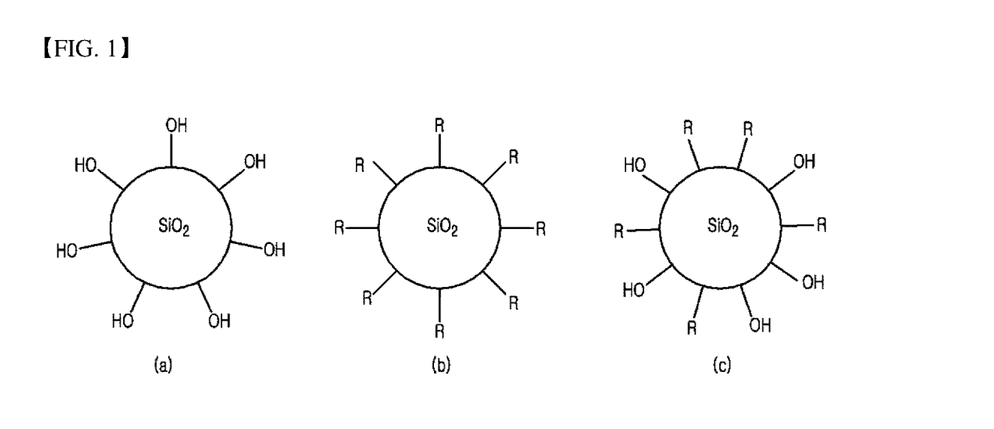
FIG. 1 is a schematic diagram briefly illustrating a hydrophilic aerogel particle, a hydrophobic aerogel particle, and a hybrid aerogel particle.

FIG. 1 is a schematic diagram briefly illustrating a hydrophilic aerogel particle, a hydrophobic aerogel particle, and a hybrid aerogel particle.

Referring to FIG. 1, a hybrid aerogel particle (c) may have both a hydrophobic functional group and a hydrophilic functional group on a surface thereof. A hydrophilic aerogel particle (a) may mainly have a hydrophilic functional group on a surface thereof. A hydrophobic aerogel particle (b) may mainly have a hydrophobic functional group on a surface thereof. In this case, the functional groups on a surface may be bonded to Si atoms, which are a component of the aerogel particle. While FIG. 1 illustrates only a case in which a surface of the particle has functional groups, the present invention is not limited thereto, and a surface of a pore inside the particle may also have the same functional groups as those on the outer surface of the particle.

The hydrophobic functional group (R) may be hydrogen, a C1 to C18 alkyl group, a silyloxy group represented by the following Chemical Formula 1, or a combination thereof.

[Chemical Formula 1]

In Chemical Formula 1,
$R^1$ is a C1 to C18 alkyl group,
n is an integer ranging from 0 to 3, and
* may denote a bond to a Si atom in an aerogel particle.

When n is an integer ranging from 1 to 3, the functional group represented by Chemical Formula 1 may be called an alkylsilyloxy group. The C1 to C18 alkyl group may be a C1 to C18 linear alkyl group or a C3 to C18 branched alkyl group. The C1 to C18 linear alkyl group may be a C1 to C6 linear alkyl group or a C1 to C6 saturated linear alkyl group, for example, a methyl, ethyl, n-propyl, n-butyl, n-pentyl, or n-hexyl group. In one embodiment, the C1 to C6 linear alkyl group may be a methyl group or an ethyl group.

Meanwhile, the hydrophilic functional group may be a hydroxy group (—OH).

The hybrid aerogel particle (c) may have a hydrophobic functional group (R) and a hydrophilic functional group (OH) on a surface thereof in a molar ratio of 8:2 to 2:8, particularly, 7:3 to 3:7. The hydrophilic aerogel particle (a) may have a hydrophilic functional group on a surface thereof at greater than 80 mol % to 100 mol %, particularly, 85 mol %, 90 mol %, 95 mol %, or 99 mol % or more. The hydrophobic aerogel particle (b) may have a hydrophobic functional group on a surface thereof at greater than 80 mol % to 100 mol %, particularly, 85 mol %, 90 mol %, 95 mol %, or 99 mol % or more.

The hybrid aerogel particle (c), the hydrophilic aerogel particle (a), and the hydrophobic aerogel particle (b) are distinguished according to affinity for water. When the aerogel particles are input into a vessel containing water, the hydrophilic aerogel particles (a) may sink to the bottom of the vessel, the hydrophobic aerogel particles (b) may float on the surface of water, and the hybrid aerogel particles (c) may be approximately half-submerged beneath the surface of water.

An aerogel particle may have a size of several micrometers to several tens of micrometers, for example, 1 to 40 μm. Also, an aerogel particle may have a surface area of 500 to 1,000 m$^2$/g as determined in accordance with the BET method.

Aerogel Powder Example 2

Aerogel powder according to another embodiment of the present invention may be similar to the aerogel powder according to Aerogel Powder Example 1 except as described below.

The aerogel powder according to Aerogel Powder Example 2 may include hydrophobic aerogel particles having a hydrophobic surface ((b) of FIG. 1) and hydrophilic aerogel particles having a hydrophilic surface ((a) of FIG. 1). The hydrophobic aerogel particles may have hydrophobicity at a surface of a pore inside the particle as well as at a surface of the particle, and the hydrophilic aerogel particles may have hydrophilicity at a surface of a pore inside the particle as well as at a surface of the particle.

In one example, the aerogel powder may be a mixture of hydrophilic aerogel particles and hydrophobic aerogel particles. This mixture may contain about 30 to 70 wt % of the hydrophilic aerogel particles and about 30 to 70 wt % of the hydrophobic aerogel particles. In one embodiment, the hydrophilic aerogel particles and the hydrophobic aerogel particles may be contained in a weight ratio of 1:1.

Surface Modification of Aerogel Powder

Surface modification of aerogel powder may be carried out using the following method, but the present invention is not limited thereto.

First, hydrophobic aerogel powder may be prepared. In this case, the hydrophobic aerogel powder may be prepared by modifying a surface of a hydrogel into a hydrophobic surface, followed by drying and grinding. Specifically, the hydrophobic aerogel powder may be prepared by preparing aerogel using a method disclosed in Korean Registered Patent No. 10-1420163 (included as a reference in the present patent) and grinding the aerogel. However, the present invention is not limited thereto.

The hydrophobic aerogel powder may be thermally treated to partially modify an outer surface of particles included therein and also partially modify a surface of a pore inside particles. Specifically, hydrophobic surface functional groups of at least some of particles included in hydrophobic aerogel powder may be converted into hydrophilic surface functional groups. More specifically, a hydrophobic surface functional group (R in FIG. 1), such as hydrogen, a C1 to C18 linear or branched alkyl group, or the silyloxy group represented by Chemical Formula 1, particularly an alkylsilyloxy group, may be converted into a hydroxy group through thermal treatment. Simultaneously, water remaining in aerogel powder may be at least partially or completely removed.

The thermal treatment of hydrophobic aerogel powder may include raising a temperature of hydrophobic aerogel powder and sintering the hydrophobic aerogel powder by maintaining it at the raised temperature for a predetermined time.

Accordingly, at least some particles of the hydrophobic aerogel powder may be converted into hybrid aerogel particles ((c) of FIG. 1) having both a hydrophobic surface and a hydrophilic surface, some of the other particles may be converted into hydrophilic aerogel particles ((a) of FIG. 1) having a hydrophilic surface, and the rest may remain as hydrophobic aerogel particles ((b) of FIG. 1) by retaining a hydrophobic surface as described above. As a result, aerogel powder which is a mixture including all of hydrophilic aerogel particles, hydrophobic aerogel particles, and hybrid aerogel particles can be obtained. In another embodiment, the entire particles of aerogel powder may be converted into hydrophilic aerogel particles ((a) of FIG. 1) having a hydrophilic surface.

When the hydrophobic aerogel includes an alkyl group, the hydrophobic aerogel may have a larger particle size, a smaller pore volume, and a lower surface area of a pore than those of hydrophilic aerogel. More specifically, as an alkyl group is oxidized to produce a hydroxy group, the size of a functional group becomes smaller so that the size of aerogel particle may be reduced and the volume and surface area of a pore may be increased. Therefore, the space capable of absorbing moisture is increased, and thus hydrophilicity may be increased, but the present invention is not limited to this theory.

The thermal treatment may be carried out using an electric furnace for 0.5 hour to 24 hours at a raised temperature of 300 to 500° C. Also, the thermal treatment may be carried out under an oxidizing atmosphere, particularly an air atmosphere. Depending on the temperature or time of thermal treatment, only some of the hydrophobic surface functional groups of the hydrophobic aerogel may be converted into hydrophilic surface functional groups or all of the hydrophobic surface functional groups of the hydrophobic aerogel may be converted into hydrophilic surface functional groups to form hydrophilic aerogel. In one example, the conversion of only some of the hydrophobic surface functional groups of the hydrophobic aerogel into hydrophilic surface functional groups may be carried out through thermal treatment at about 345 to 355° C., particularly 347 to 353° C., and the conversion of all of the hydrophobic surface functional groups of the hydrophobic aerogel into hydrophilic surface functional groups to form hydrophilic aerogel may be carried out through thermal treatment at about 356 to 365° C., particularly 357 to 363° C.

In one example, the aerogel powder according to Aerogel Powder Example 1 may be formed using a product obtained by converting only some of the hydrophobic surface functional groups of the hydrophobic aerogel into hydrophilic surface functional groups. In another example, the aerogel powder according to Example 1 may be formed by mixing hydrophilic aerogel obtained by converting all of the hydrophobic surface functional groups of the hydrophobic aerogel into hydrophilic surface functional groups, surface-unmodified hydrophobic aerogel, and aerogel particles having both hydrophilic and hydrophobic surfaces.

The aerogel powder according to Aerogel Powder Example 2 may be formed by mixing hydrophilic aerogel obtained by converting all of the hydrophobic surface functional groups of the hydrophobic aerogel into hydrophilic surface functional groups and surface-unmodified hydrophobic aerogel.

External Preparation for Skin Including Aerogel

The external preparation for skin according to an embodiment of the present invention may include aerogel powder having both hydrophobicity and hydrophilicity, and may be prepared in any formulation commonly prepared in the art.

The aerogel powder with both hydrophobicity and hydrophilicity may be formed using the aerogel powder according to Aerogel Powder Example 1, i.e., aerogel powder including hydrophilic aerogel particles, hydrophobic aerogel particles, and hybrid aerogel particles, or the aerogel powder according to Aerogel Powder Example 2, i.e., aerogel powder formed by mixing hydrophilic aerogel particles and hydrophobic aerogel particles.

Such an external preparation for skin may exhibit very excellent effects of moisturizing, sebum removal, and skin texture improvement. Such an external preparation for skin may exhibit a moisturizing effect due to abundant pores in the aerogel, i.e., a nanoporous structure, exhibit a sebum removal effect by absorbing a large volume of sebum, and also exhibit an effect of blocking ultraviolet rays through reflection of light. As a result of a combination of the above-described effects, the external preparation for skin may also exhibit an effect of improving skin texture. The external preparation for skin having these effects may protect the skin from heat and ultraviolet rays and at the same time moisturize the skin even in a hot and dry environment such as in a desert or in a cold and dry environment such as in winter.

In addition, since aerogel powder with both hydrophobicity and hydrophilicity is used, it may be appropriately mixed into the external preparation for skin, which is a hydrophobic and hydrophilic emulsion, and improve the effects accordingly.

The external preparation for skin according to an embodiment of the present invention may be formulated, for example, as a solution, a suspension, an emulsion, a paste, a gel, a cream, a lotion, powder, soap, a surfactant-containing cleanser, an oil, a powder foundation, an emulsion foundation, a wax foundation, a spray, or the like, but the present invention is not limited thereto. More specifically, the external preparation for skin may be formulated as a skin softener, a nourishing lotion, a nourishing cream, a massage cream, a skin serum, an eye cream, a cleansing cream, a cleansing foam, a cleansing water, a pack, a spray, or powder. In one example, the external preparation for skin may be in the form of a paste, and particularly, may be produced in the form of a moisturizing cream, a mask pack, a peel-off type pack, or a mask.

In one example, when the external preparation for skin according to an embodiment of the present invention is in the form of a paste, i.e., an aerogel paste, it may be prepared by mixing the above-described aerogel powder and a solvent. The solvent may be (purified) water, an alcohol such as ethanol, or a mixture thereof. In addition, the aerogel paste may further include a thickener. The thickener is for adjusting a viscosity of an aerogel paste to be prepared, and may include, for example, an ingredient such as cellulose, hydroxypropyl cellulose, gelatin, methyl cellulose, carbomers, sodium carboxymethyl cellulose, guar gum, stearic acid, polyvinyl alcohol, collagen, mannan, carrageenans, or the like.

The aerogel powder, the solvent, and the thickener may be mixed in a set ratio. In this case, the mixing ratio or mixing time of the solvent and a thickener may be suitably determined according to the amount of aerogel powder and the use of a product to be prepared.

The aerogel paste may contain a moisturizer, a functional additive, a surfactant, or a combination thereof. The moisturizer may include one or more selected from the group consisting of glycerine, propylene glycol, ethylene glycol, butylene glycol, dipropylene glycol, pentylene glycol, hexylene glycol, and sorbitol. The functional additive may be a preservative, and the preservative may include one or more selected from the group consisting of phenoxyethanol, methylparaben, ethylparaben, mineral oil, isopropyl alcohol, and a natural preservative. The surfactant may include one or more selected from the group consisting of coco-betaine, lecithin, xanthan gum, olive emulsifying wax, and LES.

For example, the aerogel paste may contain 0.001 to 10 vol % of the aerogel powder, 40 to 60 vol % of the solvent, 1 to 25 vol % of the thickener, 1 to 20 vol % of the moisturizer, 0.01 to 3 vol % of the preservative, and 0.01 to 10 vol % of the surfactant. However, it is to be understood that the solvent, the thickener, the moisturizer, the preservative, and the surfactant are not limited to the above-mentioned content ratios and may be mixed in other content ratios.

The external preparation for skin may further include a common adjuvant (e.g. a wax, an oil, a coloring agent, a flavoring agent, an antioxidant, a stabilizer, a solubilizer, a vitamin, a pigment, and a fragrance), a carrier, or the like, all of which are commonly used in a cosmetic composition, within a range which does not hinder the object of the present invention.

Such an aerogel paste may be used in an external preparation for skin or a cosmetic composition, specifically a cream, a mask pack, a peel-off type pack, or the like which is applied to the skin as described above. However, the aerogel paste is not limited thereto and may also be used for other purposes. Also, the aerogel paste may be applied onto or soaked into a thin and flexible material to produce a cosmetic product in the form of a mask. As the thin and flexible material, paper, vinyl, a non-woven fabric, or the like may be used, but the present invention is not limited thereto.

Hereinafter, exemplary experimental examples will be described for promoting understanding of the present invention. However, the following experimental examples are only examples to help understanding of the present invention, and the present invention is not limited thereto.

Aerogel Surface Modification Example 1

Hydrophobic aerogel powder having a trimethylsilyloxy group ($-OSi(CH_3)_3$) on a surface thereof, which was obtained by grinding the aerogel prepared through a method disclosed in Korean Registered Patent No. 10-1420163, was input into an electric furnace under an oxidizing atmosphere, and a temperature of the electric furnace was raised to 340°

C. Then, the hydrophobic aerogel powder was sintered for 1 hour while maintaining this temperature.

Aerogel Surface Modification Example 2

Hydrophobic aerogel powder was sintered in the same manner as in Aerogel Surface Modification Example 1 except that the sintering was carried out at 350° C.

Aerogel Surface Modification Example 3

Hydrophobic aerogel powder was sintered in the same manner as in Aerogel Surface Modification Example 1 except that the sintering was carried out at 360° C.

Figure 2A:
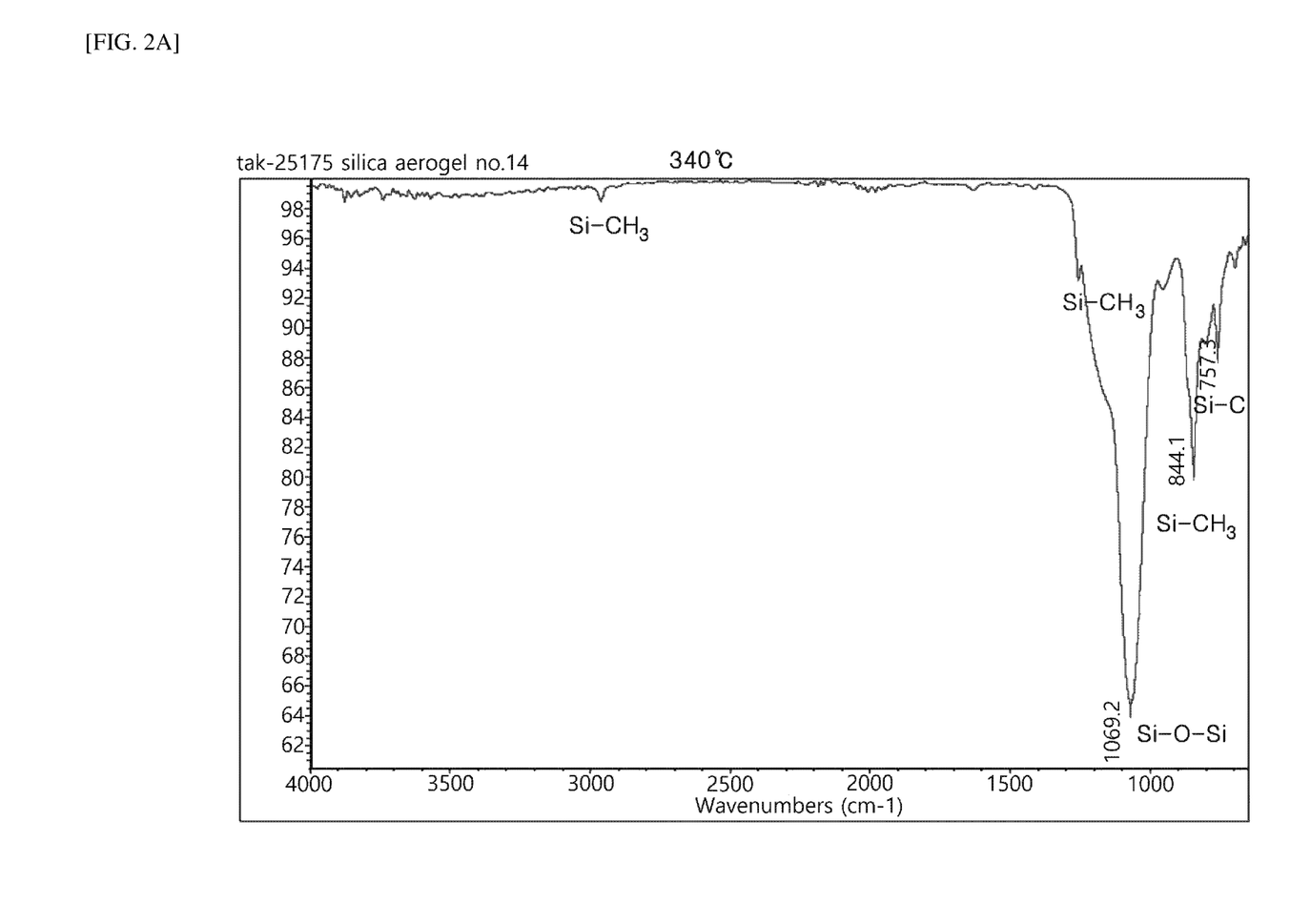
FIGS. 2A to 2C are graphs illustrating measurement results of the powders obtained in Aerogel Surface Modification Examples 1 to 3, respectively, through Fourier-transform infrared spectroscopy (FT-IR spectroscopy).
Figure 2B:
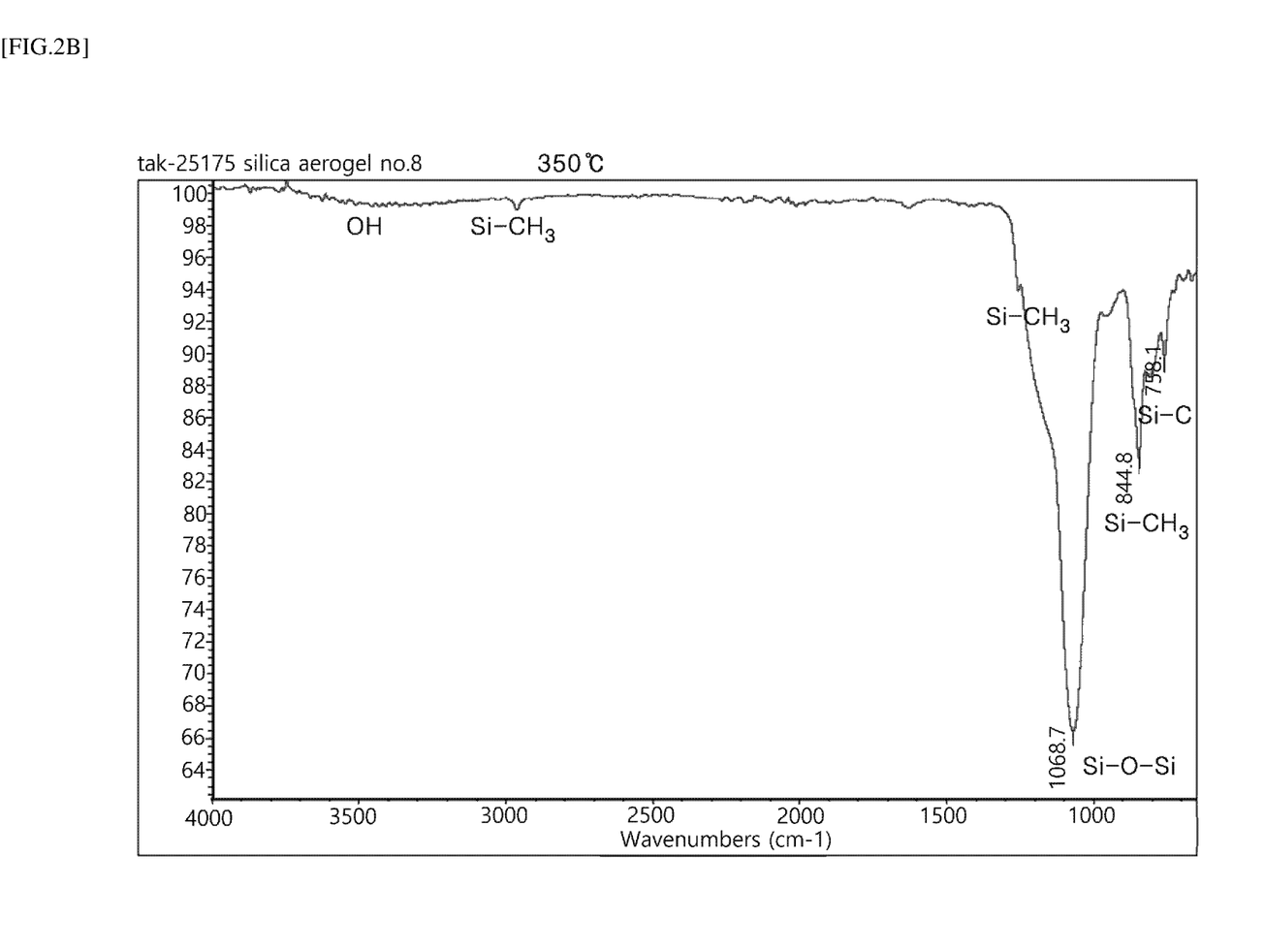
Figure 2C:
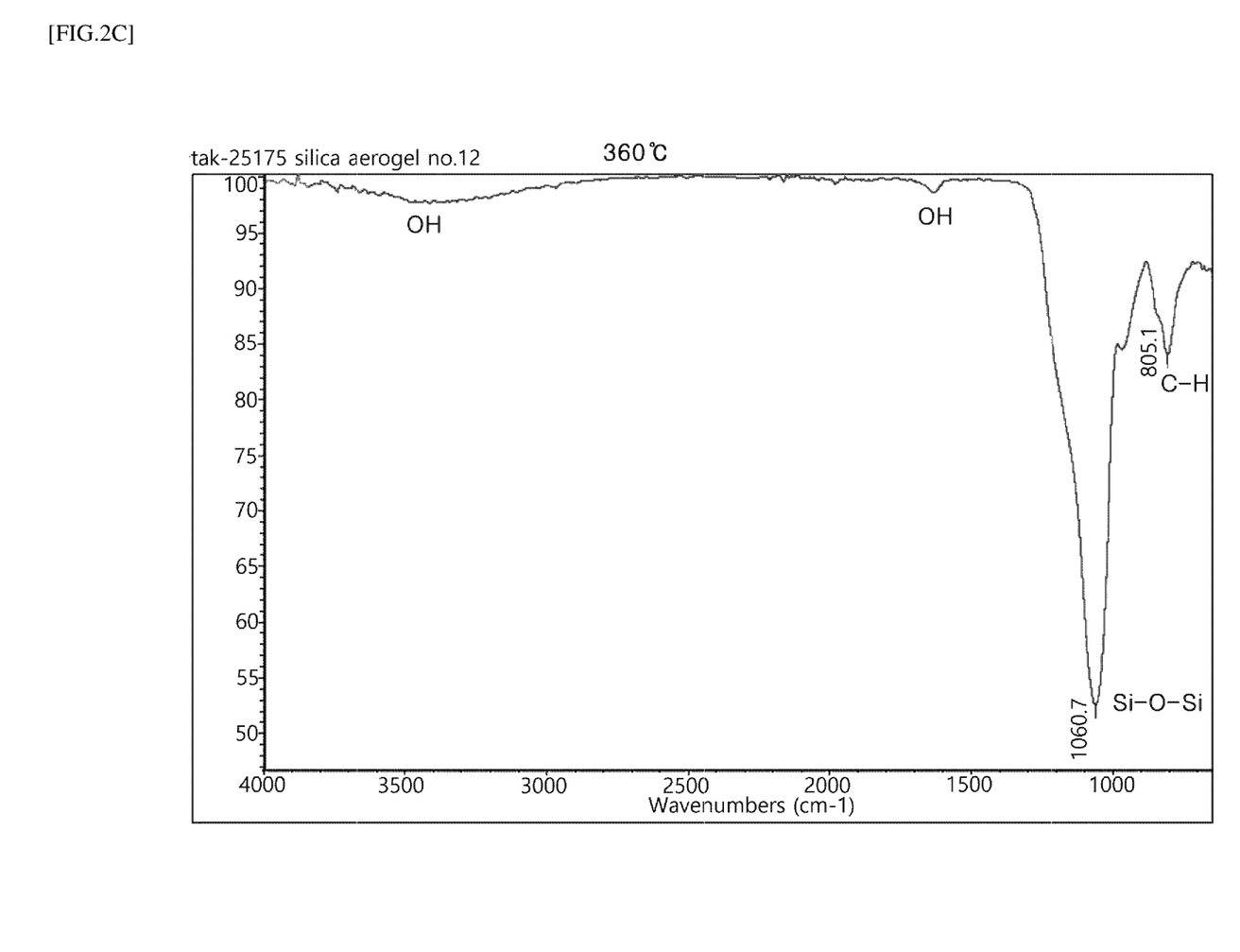

FIGS. 2A to 2C are graphs illustrating measurement results of the powders obtained in Aerogel Surface Modification Examples 1 to 3, respectively, through Fourier-transform infrared spectroscopy (FT-IR spectroscopy).

Referring to FIG. 2A, it can be seen that the aerogel according to Aerogel Surface Modification Example 1 showed a Si—$CH_3$ group in addition to a Si—O—Si group inherent in silica, indicating that the aerogel remained as hydrophobic aerogel having a hydrophobic surface despite thermal treatment.

Referring to FIG. 2B, it can be seen that the aerogel according to Aerogel Surface Modification Example 2 showed both a Si—$CH_3$ group and an OH group in addition to a Si—O—Si group inherent in silica, indicating that the aerogel was hybrid aerogel formed by partially modifying a hydrophobic surface into a hydrophilic surface through thermal treatment.

Referring to FIG. 2C, it can be seen that the aerogel according to Aerogel Surface Modification Example 3 showed an OH group in addition to a Si—O—Si group inherent in silica, and that a peak corresponding to a Si—$CH_3$ group, which had been observed before surface modification, completely disappeared, indicating that the aerogel was converted into hydrophilic aerogel formed by completely modifying a hydrophobic surface into a hydrophilic surface through thermal treatment.

Figure 3:
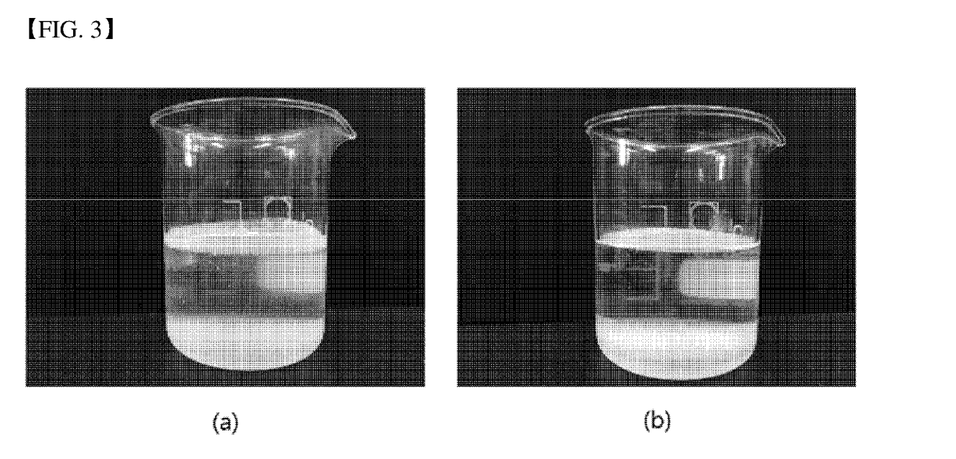
FIG. 3 is an image illustrating the floating degree of aerogel powder including hybrid aerogel according to Aerogel Surface Modification Example 2 and a mixture of hydrophilic aerogel according to Aerogel Surface Modification Example 3 and hydrophobic aerogel before surface modification of aerogel in water.

FIG. 3 is an image illustrating the floating degree of aerogel powder including hybrid aerogel according to Aerogel Surface Modification Example 2 and a mixture of hydrophilic aerogel according to Aerogel Surface Modification Example 3 and hydrophobic aerogel before surface modification of aerogel in water.

Referring to FIG. 3, it can be seen that, in the case of a mixture (b) of hydrophilic aerogel according to Aerogel Surface Modification Example 3 and hydrophobic aerogel before surface modification of aerogel, hydrophobic aerogel floating on the surface of water and hydrophilic aerogel settled in the bottom of a beaker are clearly distinguished. On the other hand, it can be seen that, in the case of aerogel powder (a) including aerogel according to Aerogel Surface Modification Example 2, aerogel particles include all of the hybrid aerogel particles approximately half-submerged beneath the surface of water, hydrophilic aerogel particles settled in the bottom of a beaker, and hydrophobic aerogel particles floating on the surface of water.

In addition, simultaneously referring to FIG. 2B and FIG. 3, it can be assumed that, in the aerogel powder according to Aerogel Surface Modification Example 2, hybrid aerogel has both a Si—$CH_3$ group and an OH group on a surface thereof, hydrophilic aerogel mainly has an OH group on a surface thereof, and hydrophobic aerogel mainly has a Si—$CH_3$ group on a surface thereof.

Additionally, each of OH peak intensities in FIGS. 2B and 2C and results of FIG. 3 collectively suggest that the aerogel powder according to Aerogel Surface Modification Example 2 may include 25 to 40 wt % of the hybrid aerogel particles, 25 to 40 wt % of the hydrophobic aerogel particles, and 25 to 40 wt % of the hydrophilic aerogel particles, and that these particles are mixed in a weight ratio of 1:1:1.

Preparation Examples of Moisturizing Cream 5 g of a moisturizing cream was mixed with 1 g of aerogel powder having a composition as shown in the following Table 1 to prepare a moisturizing cream to be tested.

TABLE 1

| Preparation Examples of moisturizing cream | Aerogel powder of Aerogel Surface Modification Example 2 (including hybrid aerogel) | Aerogel powder of Aerogel Surface Modification Example 3 (hydrophilic aerogel) | Surface-unmodified hydrophobic aerogel |
|---|---|---|---|
| Preparation Example 1 | 1 g | — | — |
| Preparation Example 2 | — | 0.5 g | 0.5 g |
| Preparation Example 3 | — | 0.6 g | 0.4 g |
| Preparation Example 4 | — | 0.7 g | 0.3 g |
| Preparation Example 5 | — | 0.8 g | 0.2 g |
| Preparation Example 6 | — | 0.9 g | 0.1 g |

Figure 4:
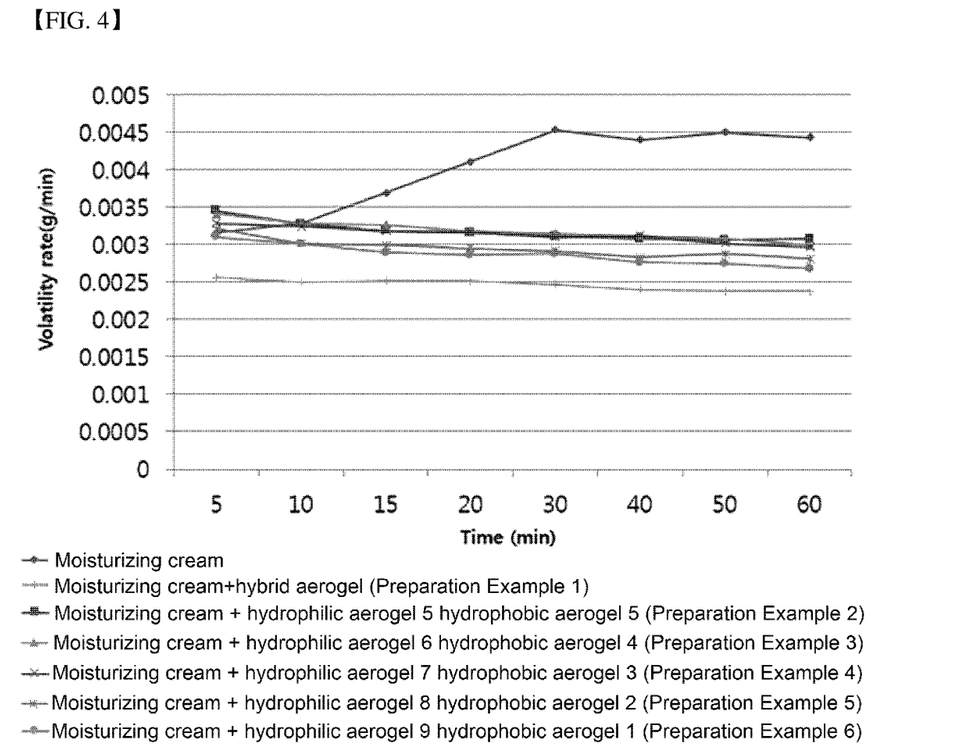
FIG. 4 is a graph illustrating changes in moisture volatility rates over time of the moisturizing cream according to any one of Preparation Examples 1 to 6 and a moisturizing cream not including aerogel.

FIG. 4 is a graph illustrating changes in moisture volatility rates over time of the moisturizing cream according to any one of Preparation Examples 1 to 6 and a moisturizing cream not including aerogel. The moisture volatility rate is calculated by measuring a change in weight of a sample (i.e., an amount of moisture evaporated) over time.

Referring to FIG. 4, for a moisturizing cream not including aerogel, there was a rapid increase in a volatility rate of moisture when more than 10 minutes had elapsed, whereas a moisturizing cream including aerogel (Preparation Examples 1 to 6) exhibited a constantly maintained volatility rate of moisture.

It can be seen that, in regards to a moisturizing cream including a mixture of hydrophilic aerogel and hydrophobic aerogel (Preparation Examples 2 to 6), a higher content of hydrophilic aerogel slightly lowers a volatility rate of moisture.

It can be seen that a moisturizing cream (Preparation Example 1) including aerogel having both a hydrophilic surface and a hydrophobic surface, i.e., hybrid aerogel, exhibited a significantly lower volatility rate of moisture compared to a moisturizing cream (Preparation Examples 2 to 6) including a mixture of hydrophilic aerogel and hydrophobic aerogel, further even compared to a moisturizing cream (Preparation Example 6) including hydrophilic aerogel and hydrophobic aerogel in a weight ratio of 9:1. Due to its advantages as described above, hybrid aerogel can provide a surprisingly excellent moisturizing effect to an external preparation for skin.

Preparation Example of Peel-Off Type Pack 5 g of a peel-off type pack was mixed with 1 g of the aerogel according to Aerogel Surface Modification Example 2.

Figure 5:
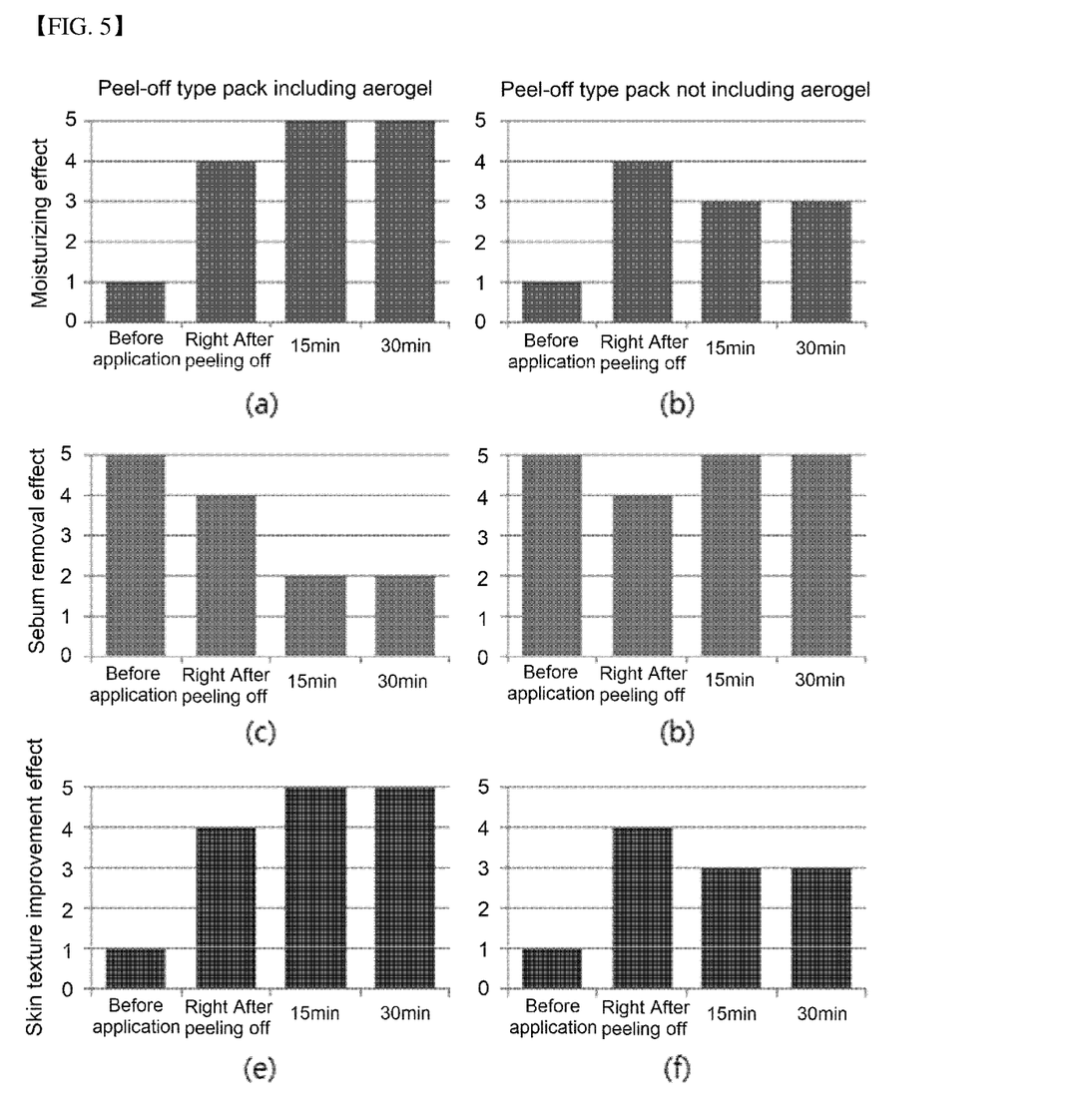
FIG. 5 is a set of graphs illustrating a moisturizing effect (a, b), an oil removal effect (c, d), and a skin texture improvement effect (e, f) of a peel-off type pack including the aerogel according to Aerogel Surface Modification Example 2 and a peel-off type pack not including aerogel.

FIG. 5 is a set of graphs illustrating a moisturizing effect (a, b), an oil removal effect (c, d), and a skin texture improvement effect (e, f) of a peel-off type pack including the aerogel according to Aerogel Surface Modification Example 2 and a peel-off type pack not including aerogel. Specifically, skin conditions before the application of a peel-off type pack ("before application"), immediately after the removal of a peel-off type pack after a predetermined time have elapsed since the application of the pack to the skin ("after removal"), and 15 minutes and 30 minutes after the removal of a peel-off type pack ("15 min" and "30 min", respectively) were measured using a skin measurement device. The measurement values of skin conditions converted based on the maximum measurement value set to 5 are shown on the y-axis.

Referring to FIG. 5, a peel-off type pack including aerogel having both a hydrophilic surface and a hydrophobic surface, i.e., hybrid aerogel, exhibited effects of moisturizing, sebum removal, and skin texture improvement similar to those of a peel-off type pack not including aerogel, immediately after the removal of the pack. However, after a predetermined time have elapsed since the removal of the packs, it can be seen that the pack including hybrid aerogel provided significantly improved effects of moisturizing, sebum removal, and skin texture improvement compared to the pack not including aerogel.

The present invention has been described in detail with reference to examples but is not limited to the examples. Also, it will be understood by those skilled in the art that various changes and modifications may be made within a range without departing from the technological spirit and the scope of the present invention.

The invention claimed is:

1. An external preparation for skin comprising:
   silica aerogel powder including a mixture of hydrophilic silica aerogel particles having a hydrophilic functional group on a surface thereof, hydrophobic silica aerogel particles having a hydrophobic functional group on a surface thereof, and hybrid silica aerogel particles having both of the hydrophilic functional group and the hydrophobic functional group on a surface thereof; and
   a solvent,
   wherein the hydrophilic functional group is a hydroxy group, and the hydrophobic functional group is hydrogen, a C1 to C18 alkyl group, a silyloxy group of the following Chemical Formula 1, or a combination thereof:

Chemical Formula 1 wherein $R^1$ is a C1 to C18 alkyl group,
   n is an integer ranging from 0 to 3, and
   * denotes a bond.

2. The external preparation for skin of claim 1, wherein the hybrid silica aerogel particles have the hydrophobic functional group and the hydrophilic functional group on a surface thereof at a molar ratio of 8:2 to 2:8.

3. The external preparation for skin of claim 1, wherein the silica aerogel powder contains 25 to 40 wt % of the hybrid silica aerogel particles, 25 to 40 wt % of the hydrophilic silica aerogel particles, and 25 to 40 wt % of the hydrophobic silica aerogel particles.

4. The external preparation for skin of claim 1, wherein the hydrophobic functional group is a silyloxy group represented by Chemical Formula 1,
   wherein n is an integer ranging from 1 to 3, and the C1 to C18 alkyl group of Chemical Formula 1 is a C1 to C6 linear alkyl group.

5. The external preparation for skin of claim 4, wherein the C1 to C6 linear alkyl group is a methyl group or an ethyl group.

6. The external preparation for skin of claim 1, further comprising at least one selected from the group consisting of a thickener, a moisturizer, a preservative, and a surfactant.

7. The external preparation for skin of claim 1, wherein the external preparation for skin is a moisturizing cream or a peel-off type pack.

8. An aerogel paste comprising:
   silica aerogel powder exhibiting all of a Si—O—Si group, a Si—CH$_3$ group, and an OH group in a Fourier transform infrared (FT-IR) spectroscopic graph, wherein the silica aerogel powder contains hybrid silica aerogel particles having both a Si—CH$_3$ group and an OH group on a surface thereof, hydrophobic silica aerogel particles having a Si—CH$_3$ group on a surface thereof, and hydrophilic silica aerogel particles having an OH group on a surface thereof; and
   a solvent.

9. The aerogel paste of claim 8, wherein the silica aerogel powder contains 25 to 40 wt % of the hybrid silica aerogel particles, 25 to 40 wt % of the hydrophobic silica aerogel particles, and 25 to 40 wt % of the hydrophilic silica aerogel particles.

10. The aerogel paste of claim 8, wherein the solvent is water, an alcohol, or a combination thereof.

11. A method of preparing an external preparation for skin, the method comprising:
    mixing silica aerogel powder with a solvent to obtain an aerogel paste, said silica aerogel powder including hydrophilic silica aerogel particles having a hydrophilic functional group on a surface thereof, hydrophobic silica aerogel particles having a hydrophobic functional group on a surface thereof, and hybrid silica aerogel particles having both of the hydrophilic functional group and the hydrophobic functional group on a surface thereof,
    wherein the hydrophilic functional group is a hydroxy group, and the hydrophobic functional group is hydrogen, a C1 to C18 alkyl group, a silyloxy group of the following Chemical Formula 1, or a combination thereof:

Chemical Formula 1 wherein $R^1$ is a C1 to C18 alkyl group,
    n is an integer ranging from 0 to 3, and
    * denotes a bond.

* * * * *